United States Patent [19]

Hayashi

[11] Patent Number: 5,246,669
[45] Date of Patent: Sep. 21, 1993

[54] SAMPLING BOTTLE

[75] Inventor: Hiroaki Hayashi, Konosu, Japan

[73] Assignee: Toyo Seikan Kaisha, Ltd., Tokyo, Japan

[21] Appl. No.: 848,410

[22] Filed: Mar. 6, 1992

[30] Foreign Application Priority Data

Mar. 8, 1991 [JP] Japan .................................. 3-20790[U]
Sep. 20, 1991 [JP] Japan .................................. 3-84390[U]

[51] Int. Cl.$^5$ ........................................... G01F 11/10
[52] U.S. Cl. ................................. 422/101; 73/864.41;
128/757; 422/61; 422/102; 436/66
[58] Field of Search ....................... 422/58, 61, 99–102;
436/66; 128/757; 73/864.41

[56] References Cited

U.S. PATENT DOCUMENTS

| | | | |
|---|---|---|---|
| 4,849,173 | 7/1989 | Chang | 422/101 X |
| 4,859,610 | 8/1989 | Maggio | 422/102 X |
| 5,149,506 | 9/1992 | Skiba et al. | 422/102 |

Primary Examiner—Jill A. Johnston
Attorney, Agent, or Firm—Martin A. Farber

[57] ABSTRACT

Provided is a sampling bottle with easy handling of dejection sample, simple structure, reliable prevention of scattering dejection sample and propagation of offensive smell to nearby environments, and good quantitative precision. The sampling bottle has a bottle main body having an open bottom end and a nozzle unit closed by a thin wall capable of being opened, the bottle main body being capable of containing test liquid, and a sample holding unit insertable into the bottle main body from the open bottom end. The sample holding unit has an inner plug and a sample pickup rod. The sample pickup rod is pierced into sample dejection. The sample pickup rod with attached dejection is inserted into the inner plug. Excessive sample attached to the outer surface of the sample pickup rod is scraped off by the scrape section. The scraped, excessive sample is accommodated and sealed within an excessive sample room between the inner plug and the sample pickup rod. The sample holding section is aligned with the windows of the inner plug, and the sample attached to the top end of the sample pickup rod is sealed within the top inner space of the inner plug.

5 Claims, 8 Drawing Sheets

SAMPLING BOTTLE

BACKGROUND OF THE INVENTION

The present invention relates to a sampling bottle used for picking up dejection as a sample to be tested and holding it within the bottle which contains test liquid.

DESCRIPTION OF THE RELATED BACKGROUND ART

Dejection is a good reflection of the conditions of physiology and pathology. It is therefore used as a sample for non-invasive biopsy of the conditions of physiology and pathology. Although dejection is a good test sample, care must be taken during its handling so as not to scatter it and not to allow its offensive smell to propagate to nearby environments.

Generally, a picked-up sample of dejection is suspended within test liquid, and the suspended solution is filtered to use it as a sample to be tested. Important is a good quantitative precision of picked-up dejection. If the quantity of dejection suspended within test liquid is too large or small, a good test cannot be expected.

As a technique aiming at a good quantitative precision of picked-up sample, there is a technique disclosed, for example, in Japanese Utility Model Laid-open Publication No. 64-42454. A dejection bottle described in this Publication is constructed of a bottle main body, a pickup rod, a cap, and a dispensing section. The bottle main body contains liquid for suspending dejection. The pickup rod is formed near at its bottom end at lest one of a notch, recess, and through-hole. The cap is liquid tightly connectable to the bottle main body. The dispensing unit has therein a filter. A stocker section is defined by the cap, a partition wall for partitioning the inside of the bottle main body into two rooms, and the pickup rod penetrating through the partition wall. An excessive dejection sample attached to the outer surface of the pickup rod is scraped off by the partition wall when the rod penetrates through the partition wall. The scraped dejection sample is stored in the stocker section. In this manner, the quantity of sample to be suspended within test liquid is set to that of sample held in the notch, recess or through hole, thereby ensuring a good quantitative precision of the sample.

Such a conventional technique uses the cap as one of members defining the stocker section. Therefore, it is necessary to provide a high precision liquid tight structure, or sealing structure, between the large diameter bottle main body and the cap so as to liquid tightly hold a sample. It arises therefore a problem of complicated steps of manufacturing a bottle. Furthermore, an excessive sample attached to the outer surface of the pickup rod can be scraped when the rod penetrates through the partition wall, but a sample attached to the top of the pickup rod cannot be scraped by the partition wall. Therefore, in addition to the sample held within the notch, recess, or through hole, the sample attached to the top of the rod is suspended within test liquid, being unable to achieve a good quantitative precision sample.

SUMMARY OF THE INVENTION

The present invention has been made in consideration of the above problems. It is therefore an object of the present invention to provide a sampling bottle with easy handling of dejection sample, simple structure, reliable prevention of scattering dejection sample and propagation of offensive smell to nearby environments, and good quantitative precision.

In order to achieve the above object, according to one aspect of the present invention, there is provided a sampling bottle comprising:

a bottle main body having an open bottom end and a nozzle unit closed by a thin wall capable of being opened, the bottle main body being capable of containing test liquid; and a sample holding unit insertable into the bottle main body from the open bottom end, the sample holding unit having an inner plug and a sample pickup rod, the inner plug being of a tubular shape having a large diameter section adapted to be liquid tightly fitted to the inner surface of the torso section of the bottle main body and a small diameter section having an outer diameter smaller than the large diameter section, both being integrally coupled via a shoulder section, a top end of the small diameter section being close and a bottom end of the large diameter section being open, and at least one window being formed in the wall of the small diameter section between the top end and bottom end of the smaller diameter section, the inner surface of the small diameter section of the inner plug being formed with an annular projection of the bottom end side, and an annular scrape section and an annular top sealing section near the at least one window.

the sample pickup rod having a small diameter pickup rod section and a large diameter holding section, both integrally coupled in the axial direction via a shoulder section, the pickup rod section having a projection at a bottom end portion and a sample pickup section at a top end portion, the sample pickup section comprising a sample holding section of a one-side open recess, and a scrape section and a top sealing section both defining the border of the recess, wherein at the maximum insertion position of the sample pickup rod in the inner plug, the scrape section of the inner plug becomes in contact with the scrape section of the sample pickup section of the pickup rod section to close the end of an annular excessive sample room formed in the axial direction between the inner surface of the inner plug and the outer surface of the pickup rod section, and the top sealing section liquid tightly seals a top end of the pickup rod section within a space formed at the top end portion of the inner plug.

According to another aspect of the present invention, there is provided a sample bottle comprising:

a bottle main body having an open bottom end and a nozzle unit closed by a thin wall capable of being opened, the bottle main body being capable of containing test liquid; and a sample holding unit capable of being inserted into said the bottle main body from the open bottom end, the sample holding unit having an inner plug and a sample pickup rod, the inner plug being of a tubular shape having a large diameter section adapted to be liquid tightly fitted to the inner surface of the torso section of the bottle main body and a small diameter section having an outer diameter smaller than the large diameter section, both being integrally coupled via a shoulder section, a top end of the small diameter section being close and a bottom end of the large diameter section being open, and at least one window being formed in the wall of the small diameter section between the top end and bottom end of the smaller diameter section, the inner surface of the small diameter section of the inner plug being formed with a scrape section between the top end of the small diameter section of the inner plug and the at least one window, the sample pickup rod having a small diameter pickup rod section and a large diameter holding section, both integrally coupled in the axial direction via a shoulder section, the pickup rod section having a sample pickup section at a top end portion, the sample pickup section comprising a one-side open recess, the sample pickup section has a dimension allowing to liquid tightly fit to the scrape section of the inner plug, and the large diameter section of the inner plug being formed with an air vent, wherein at the maximum insertion position of the sample pickup rod in the inner plug, the scrape section of the inner plug becomes in contact with the sample pickup section of the sample pickup rod to close the end of an annular excessive sample room formed in the axial direction between the inner surface of the inner plug and the outer surface of the pickup rod section, and the top sealing section liquid tightly seals a top end of the pickup rod section within a space formed at the top end portion of the inner plug.

In use of the sampling bottle constructed as above, the sample pickup rod is removed from the assembly of the bottle main body, inner plug, and sample pickup rod, and pierced into sample dejection. The sample pickup rod with attached dejection is inserted into the inner plug. Excessive sample attached to the outer surface of the sample pickup rod is scraped off by the scrape section. The scraped, excessive sample is accommodated and sealed within an excessive sample room between the inner plug and the sample pickup rod. The sample holding section is aligned with the windows of the inner plug, and the sample attached to the top end of the sample pickup rod is sealed within the top inner space of the inner plug. In tis manner, a predetermined quantity of the sample held in the sample holding section can be made in contact with test liquid through the windows and suspended in the test liquid.

DESCRIPTION OF THE PREFERRED EMBODIMENTS

The embodiments of the present invention will be described with reference to the accompanying drawings.

Figure 1:
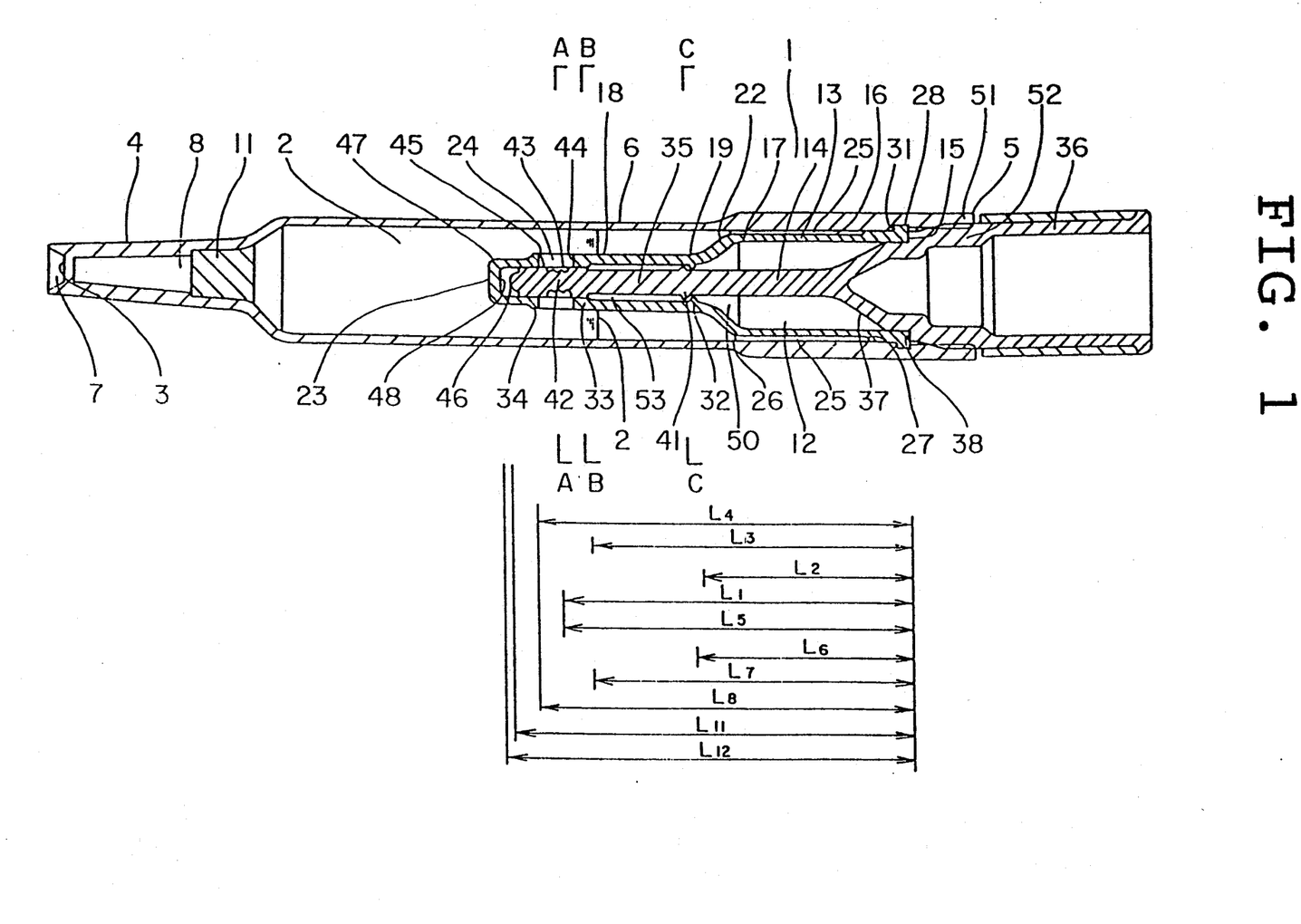
FIG. 1 is a lateral cross sectional view of a sampling bottle according to a first embodiment of the present invention.
Figure 2:
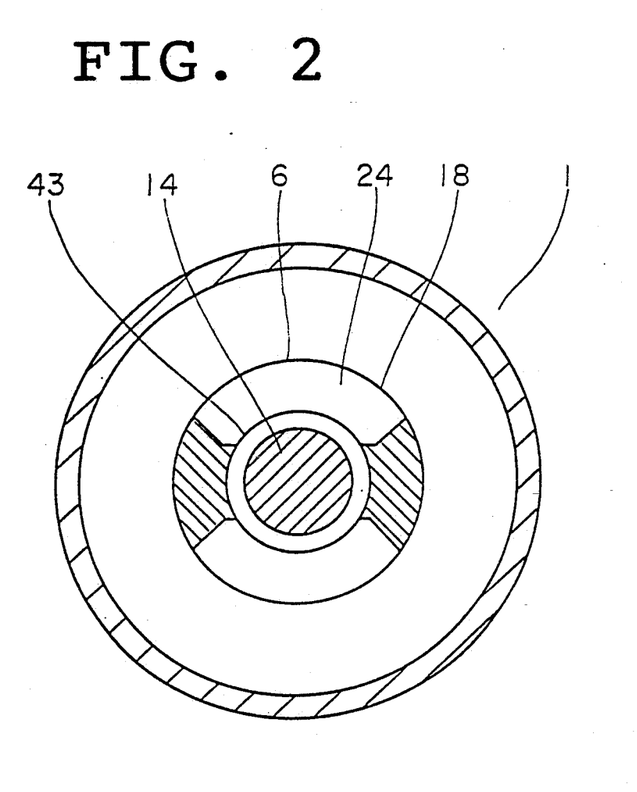
FIG. 2 is an enlarged cross sectional view taken along line A—A of FIG. 1.

In FIG. 1 and 2, reference numeral 1 represents a sampling bottle.

The sampling bottle 1 is constructed of a bottle main body 6 having an open bottom end 5, and a sample holding unit 12 insertable into the bottle main body 6 from the open bottom end 5.

The bottle main body 6 can contain test liquid 2. The bottle main body 6 has at its top end a nozzle unit 4 closed by a thin wall 3 which is destructable for opening. A filter 11 is mounted in a liquid path 8 extending to an outlet 7 of the nozzle unit 4. The sample holding unit 12 is constructed of an inner plug 13 and a sample pickup rod 14. The inner plug 13 is of a tubular shape and open at its bottom end 15. A top end 17 of a large diameter section 16 is integrally coupled via a shoulder section 22 to a bottom end 19 of a small diameter section 18. A top end 23 of the small diameter section 18 is closed and the bottom end 15 of the large diameter section 16 is open.

Two windows are formed in the wall of the small diameter section 18 at a distance L1 from the bottom end 15 between the top end 23 and bottom end 19 of the small diameter section 18.

The outer diameter of the small diameter section 18 is smaller than the inner diameter of the bottle main body 6 at its torso section. The outer diameter of the large diameter section 16 is set such that the large diameter section 16 is liquid tightly fitted to the inner surface of the bottle main body 6 at its torso section. The large diameter section 16 has at its outer surface a groove 25 formed in the axial direction. A top end 26 in the axial direction of the groove 25 is open, and a bottom end 27 thereof is closed.

A positioning ring 28 like a flange is extruded from the bottom end 15 of the large diameter section 16. A positioning step 31 is formed at the inner surface near the open bottom end 5 of the bottle main body 6. The maximum insertion position of the inner plug 13 within the bottle main body 6 is determined by the abutment of the positioning ring 28 with the positioning step 31 of the bottle main body 6.

The inner surface of the small diameter section 18 of the inner plug 13 is formed with an annular projection 32 at a distance L2 from the bottom end 15, a scrape section 33 at a distance L3, and a top sealing section 34 of a cap shape at a distance L4.

Figure 3:
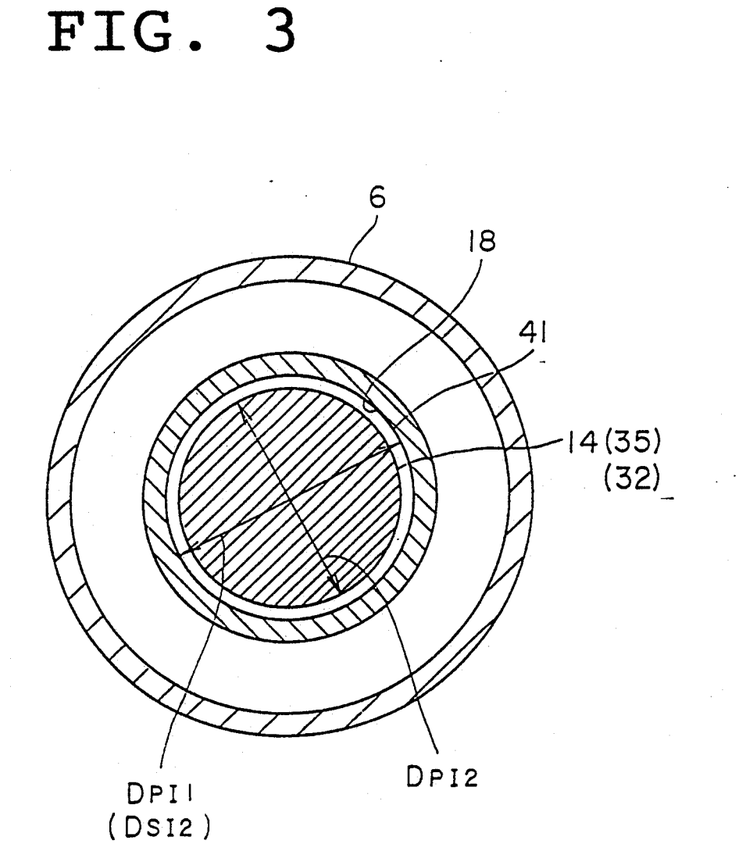
FIG. 3 is an enlarged cross sectional view taken along line C—C of FIG. 1.

As shown in FIG. 3, the annular projection 32 is located near the bottom end 19 of the small diameter section 18, and the inner diameter DPI2 of the annular projection 32 is smaller than the inner diameter DPI1 of the small diameter section 18. Namely, the inner circumference of the annular projection 32 is projected inside of the inner circumference of the small diameter section 18 by DPI1−DPI2. FIG. 3 shows only the dimensional relation.

Figure 4:
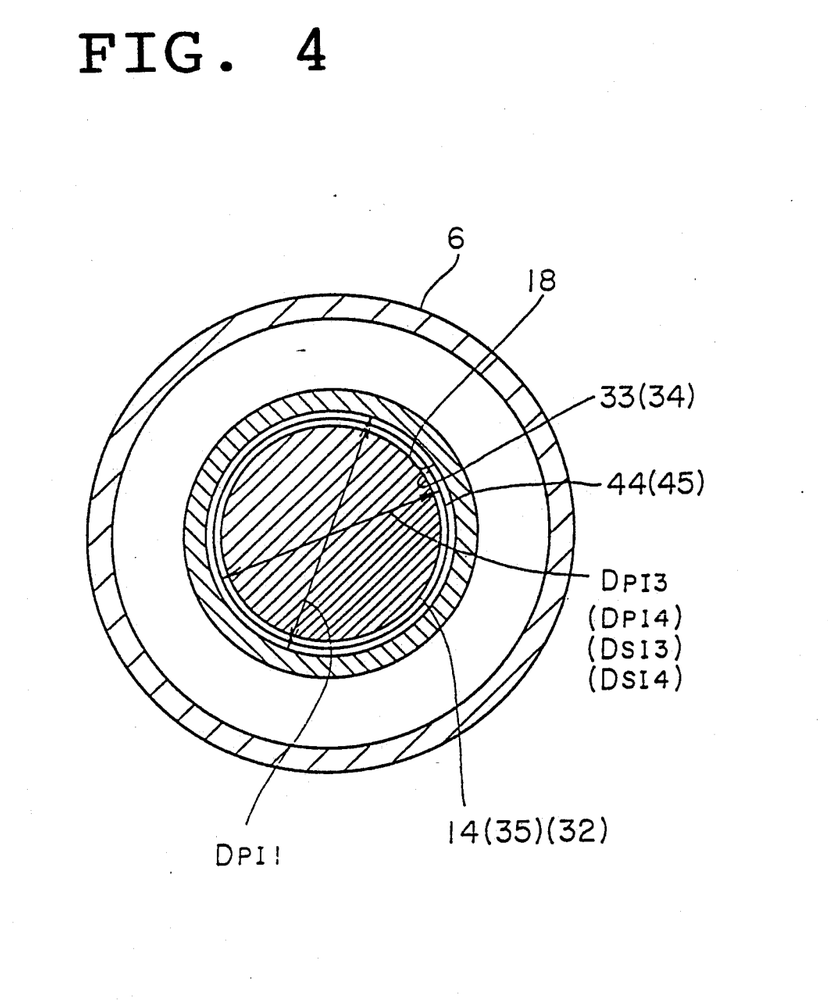
FIG. 4 is an enlarged cross sectional view taken along line B—B of FIG. 1.

As shown in FIG. 4, the scrape section 33 is located adjacent the windows 24 of the small diameter section 18 on the bottom end side, to thereby define the border of the windows. The inner diameter DPI3 of the scrape section 33 is smaller than the inner diameter DPI1 of the small diameter section 18. Namely, the inner circumference of the scrape section 33 is projected inside of the inner circumference of the small diameter section 18 by DPI1−DPUI3. FIG. 4 shows only the dimensional relation.

The top sealing section 34 is located adjacent the windows 24 of the small diameter section 18 on the top end side, to thereby define the border of the windows 24 in cooperation with the scrape section 33. The inner diameter DPI4 of the top sealing section 34 is smaller than the inner diameter DPI1 of the small diameter section 18. Namely, the inner circumference of the top sealing section 34 is projected inside of the inner circumference of the small diameter section 18 by DPI1−−DPI4.

Accordingly, the scrape section 33 and top sealing section 34 face each other in the axial direction of the small diameter section 18, with the windows 24 being interposed therebetween.

The sample pickup rod 14 is constructed of a small diameter pickup rod section 35 and a large diameter holding section 36, both integrally coupled in the axial direction via a shoulder section 37.

The small diameter pickup rod section 35 is insertable into the inner plug 13. The maximum insertion position of the sample pickup rod 14 within the inner plug 13 is determined by the abutment of a positioning step 38 formed on the outer periphery of the large diameter holding section 36 at its top end portion, with the positioning ring 28 of the inner plug 13.

The small diameter pickup rod section 35 has a plurality of projections 41 at a distance L6 from the positioning step 38, and a sample pickup section 42 near the top end. The sample pickup section 42 is constructed of a sample holding section 43, a scrape section 44, and a top sealing section 45. The sample holding section 43 is formed with a one-side open recess on the surface of the sample pickup section 42. The scrape section 44 and top sealing section 45 define the border of the sample holding section 43.

The sample holding section 43 is located at a distance L5 from the positioning step 38. The scrape section 44 is located at a distance L7. The top sealing section 45 is located at a distance L8. The position L6 of the projections 41 of the small diameter pickup rod section 35 and the position L2 of the annular projection 32 of the inner plug 13 are substantially the same or the distance L6 is greater than the distance L2. Therefore, at the maximum insertion position of the sample pickup rod 14, the annular projections 41 and the annular projection 32 abut together in the axial direction.

The position L5 of the sample holding section 43 and the position L1 of the windows are substantially the same. Therefore, at the maximum insertion position of the sample pickup rod, the sample holding section 43 and the windows 24 are aligned at the same position in the axial direction.

The position L8 of the top sealing section 45 and the position L4 of the top sealing section 34 are substantially the same. Therefore, at the maximum insertion position of the sample pickup rod 14, the top sealing section 45 and the top sealing section 34 are aligned at the same position in the axial direction.

As shown in FIG. 3, the outer diameter DSI2 of the projections 41 at their apexes is larger than the inner diameter DPI2 of the annular projection 32 at its apex.

The outer diameter DSI3 of the scrape section 44 is set such that this section 44 is tightly fitted to the inner circumference (DPI3) of the scrape section 33.

The outer diameter DSI4 of the top sealing section 45 is set such that this section 45 is tightly fitted to the inner circumference (DPI4) of the top sealing section 34.

The position L11 of the top end 46 of the sample pickup rod 14 is set shorter than the position L12 of the top end 48 of an inner space 47 of the small diameter section 18. Therefore, at the maximum insertion position, a gap L12−L11 is formed between both the top ends 46 and 48.

The top end portion 52 of the large diameter holding section 36 of the sample pickup rod 14 has a dimension allowing the top end portion 52 to be tightly fitted to the inner circumference of the bottom end portion 51 of the bottle main body 6.

Next, the sampling bottle constructed as above will be described how it is treated in use.

In assembling the sample holding unit of the sample bottle, air which is compressed upon insertion of the sample holding unit into the bottle main body 6, is discharged out of the bottle main body 6 through the groove 25 until the sample holding unit 12 is completely inserted into the bottle main body 6. Upon complete insertion of the sample holding unit 12 into the bottle main body 6, the groove 25 is closed by the inner surface of the bottle main body 6 with the positioning ring 28 of the inner plug 13 being abutted with the positioning step 31 of the bottle main body 6.

The sample pickup rod 14 is dismounted from an assembly of the small diameter bottle main body 6, inner plug 13, and sample pickup rod 14. Then, the pickup rod section 35 of the sample pickup rod 14 is pierced into sample dejection and pulled out of it. The sample pickup rod 14 with sample dejection being attached thereto is inserted into the inner plug 13. In the course of inserting the sample pickup rod 14 up to the maximum insertion position, the excessive sample attached to the outer periphery of the sample pickup rod 14 is scraped off by the scrape section 33. The scraped, excessive sample is accommodated within an excessive sample room 53 between the small diameter section 18 of the inner plug 13 and the small diameter pickup rod 35 of the sample pickup rod 14, and within an excessive sample room 50 between the large diameter section 16 of the inner plug 13 and the small diameter pickup rod section 35 of the sample pickup rod 14. There is only a predetermined quantity of sample held in the sample holding section 43 of the sample pickup rod 14, and an excessive sample attached to the top end of the pickup rod section.

When the small diameter pickup rod section 35 reaches the maximum insertion position, the sample holding section 43 is aligned with the windows 24 of the inner plug 13. In this state, the sample attached to the top end 46 of the small diameter pickup rod section 35 is sealed within the inner space 47 of the inner plug 13. The opposite ends in the axial direction of the excessive sample room 53 are closed by the abutment of the annular projection 32 with the annular projections 41 and by the abutment of the scrape section 33 with the scrape section 44, so that part of the excessive sample is liquid tightly sealed within the excessive sample room 53.

The opposite ends in the axial direction of the excessive sample room 50 are closed by the tight contact of the annular projection 32 with the annular projections 41 and by the tight contact of the bottom end portion of the large diameter section 16 with bottom end portion of the large diameter holding section 36, so that part of the excessive sample is liquid tightly sealed also within the excessive sample room 50. In this manner, only the predetermined quantity of the sample held at the sample holding section 43 becomes in contact with test liquid 2 and is suspended within it. In this state wherein the sample pickup rod 14 is inserted into the inner plug of the bottle main body 6 up to its maximum insertion position, the top end portion 52 of the large diameter holding section 36 of the sample pickup rod 14 is tightly fitted to the inner surface of the bottom end portion 51 of the bottle main body 6.

In the above manner, it is possible to make only the predetermined quantity of the sample held at the sample holding section 43 contact with test liquid 2 and be suspended in it. By piercing a pin or the like through the thin wall 3 at the outlet of the nozzle unit 4, this sample-suspended solution can be discharged out of the bottle main body after passing through the filter 11.

According to the sample bottle of this invention, when the projections 41 of the sample pickup rod ride and pass over the annular projection 32 of the projections 41 while the sample pickup rod with attached sample is inserted into the inner plug, light sounds are generated to notify that the sample pickup rod has been completely inserted into the inner plug. The excessive sample attached to the outer surface of the sample pickup rod 14 inserted into the bottle main body 6 containing test liquid 2, is scraped off by the scrape sections 33 and sealed within the excessive sample rooms 53 between the inner plug 13 and the sample pickup rod 14. The excessive sample attached to the top end of the sample pickup rod 14 is sealed within the inner space 47 of the inner plug 13. Accordingly, only the predetermined quantity of the sample held in the sample holding section 43 can contact with the test liquid 2 and suspended in it.

As described above, a good quantitative precision of sample can be realized. Excessive sample is sealed within the excessive sample rooms 53 and the inner space 47 of the inner plug 13. Therefore, the excessive sample will not be suspended in test liquid 2 and leaked externally. Furthermore, the rooms and space for sealing excessive sample are formed by the two members, inner plug 13 and sample pickup rod 14 allowing a simple structure of sealing.

Next, a sampling bottle of a second embodiment will be described.

The sampling bottle 1 of the first embodiment has various advantages such as easy handling of dejection sample, simple structure, reliable prevention of scattering dejection sample and propagation of offensive smell to nearby environments, and good quantitative precision. However, the bottle main body 6 is structured to be completely closed by the inner plug 13. Therefore, if used a bottle main body 6 having a relatively small inner capacity as compared to the volume of the sample pickup rod 14, a positive pressure may be generated within the bottle main body 6 in some cases when the sample pickup rod 14 with a picked-up sample is re-inserted into the inner plug 13. In such cases, when an inspector opens the outlet 7 of the nozzle unit 4 for sample testing, there is a fear that the sample-suspended solution within the bottle main body 6 is ejected out by the positive pressure and scattered to nearby environments. Furthermore, if sample dejection is fluid or liquid, it may be pushed back out of the bottle main body 6 by the positive pressure when the sample pickup rod 14 is inserted, resulting in a variation in the quantity of sample dejection.

The sampling bottle of the second embodiment solves such problems. Even if a bottle main body is used which has a relatively small inner capacity as compared to the volume of the sample pickup rod, the positive pressure to be generated upon insertion of the sample pickup rod can be reduced, providing the sample bottle preventing scattering suspended solution and pushing back sample dejection out of the bottle main body.

Figure 5:
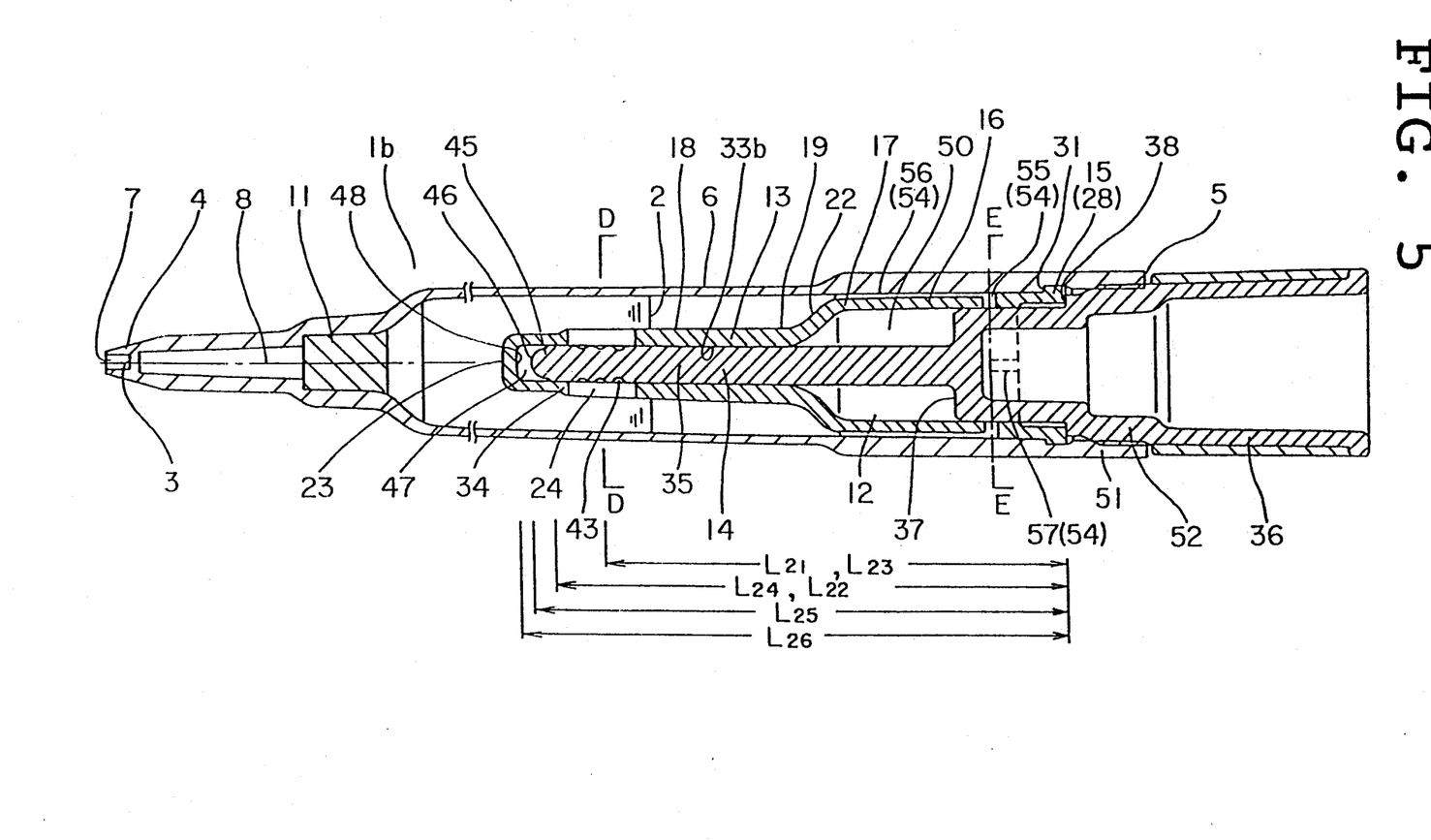
FIG. 5 is a lateral cross sectional view of a sampling bottle according to a second embodiment of the present invention.
Figure 6:
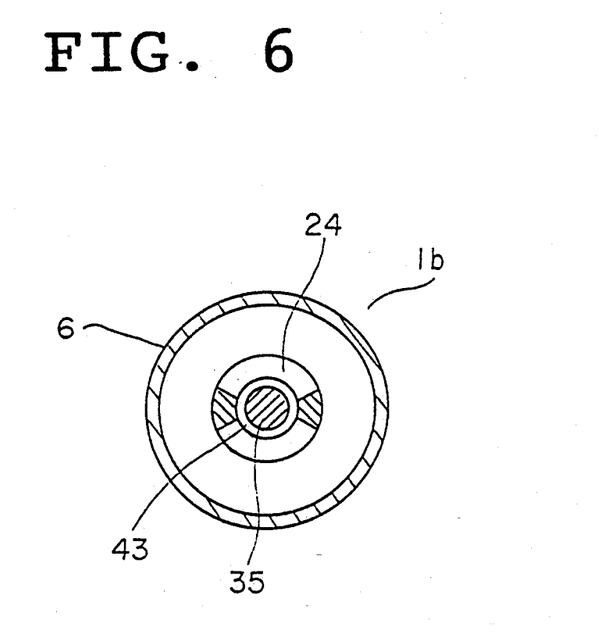
FIG. 6 is an enlarged cross sectional view taken along line D—D of FIG. 5.

In FIGS. 5 and 6, reference numeral 1b represents a sample bottle.

The sampling bottle 1b is constructed of a bottle main body 6 having an open bottom end 5, and a sample holding unit 12 insertable into the bottle main body 6 from the open bottom end 5.

Figure 7:
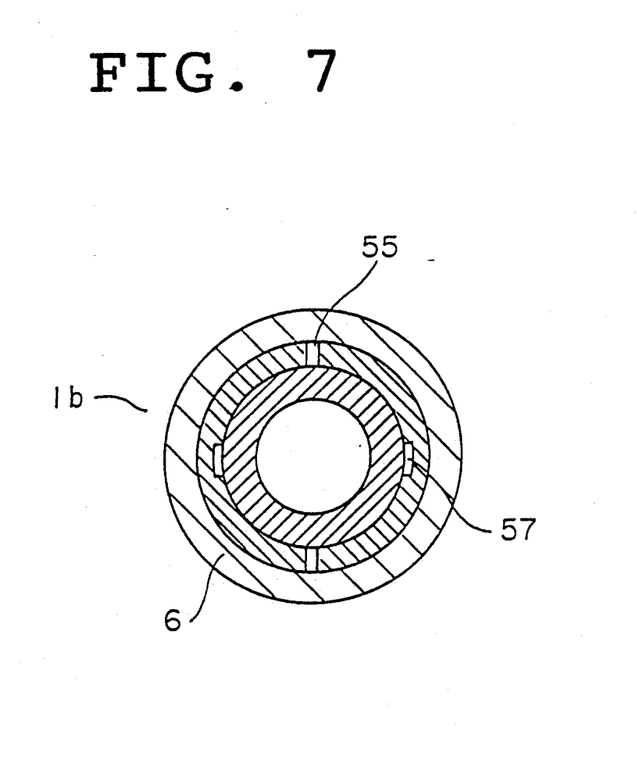
FIG. 7 is an enlarged cross sectional view taken along line E—E of FIG. 5.

The bottle main body 6 can contain test liquid 2. The bottle main body 6 has at its top end a nozzle unit 4 closed by a thin wall 3 which is destructable to open. A filter 11 is mounted in a liquid path 8 extending to an outlet 7 of the nozzle unit 4. The sample holding unit 2 is constructed of an inner plug 13 and a sample pickup rod 14. The inner plug 13 is of a tubular shape and open at its bottom end 15. A top end 17 of a large diameter section 16 is integrally coupled via a shoulder section to a bottom end 15 of a small diameter section 18. A top end 23 of the small diameter section 18 is close and the bottom end 15 of the large diameter section 16 is open. An air vent 54 is provided at the large diameter section 16. This air vent 54 is constructed of two through holes 55, and external groove 56, and two internal grooves 57. The through holes 55 are formed in the wall of the large diameter section 16 at diametrically opposing two positions of the wall. The external groove 56 is formed over the outer surface of the large diameter section 16, and the internal grooves 57 are formed on the inner surface of the wall of the large diameter section 16. The top end of the external groove 56 in the axial direction is open, and the bottom end thereof communicates with the through holes 55. The top end of the internal grooves 57 in the axial direction is close at the plane along line E—E, and the bottom end thereof is open at the position corresponding to the bottom end of the large diameter section 16. The top end of the internal grooves 57 in the axial direction is displaced by 90 degrees from the through holes 55 as viewed from the plane along line E—E.

Two windows are formed in the wall of the small diameter section 18 at a distance L23 from the bottom end 15 between the top end 23 and bottom end 19 of the smaller diameter section 18.

The outer diameter of the small diameter section 18 is smaller than the inner diameter of the bottle main body 6 at its torso section. The outer diameter of the large diameter section 16 is set such that the large diameter section 16 is liquid tightly fitted to the inner surface of the bottle main body 6 at its torso section.

A positioning ring 28 like a flange is extruded from the bottom end 15 of the large diameter section 16. A positioning step 31 is formed at the inner surface near the bottom end 5 of the bottle main body 6. The maximum insertion position of the inner plug 13 within the bottle main body 6 is determined by the abutment of the positioning ring 28 with the positioning step 31 of the bottle main body 6.

The inner surface of the small diameter section 18 of the inner plug 13 is formed with an annular scrape section 33b.

The top sealing section 34 is located adjacent the windows 24 of the small diameter section 18 on the top end side, to thereby define the border of the windows 24 in cooperation with annular scrape section 33b.

Accordingly, annular scrape section 33b and top sealing section 34 face each other in the axial direction of the small diameter section 18, with the windows 24 being interposed therebetween.

The sample pickup rod 14 is constructed of a small diameter pickup rod section 35 and a large diameter holding section 36, both integrally coupled in the axial direction via a shoulder section 37.

The small diameter pickup rod section 35 is insertable into the inner plug 13. The maximum insertion position of the sample pickup rod 14 within the inner plug 13 is determined by the abutment of a positioning step 38 formed on the outer periphery of the large diameter holding section 36 at its top end portion, with the positioning ring 28 of the inner plug 13.

The small diameter pickup rod section 35 has a sample holding section 43 and a top sealing section 45, respectively near its top end portion. The sample holding section 43 is formed with a one-side open recess.

The sample holding section 43 is located at a distance L21 from the positioning step 38. The top sealing section 45 is located at a distance L22.

The position L21 of the sample holding section 43 and the position L23 of the windows are substantially the same. Therefore, at the maximum insertion position of the sample pickup rod, the sample holding section 43 and the windows 24 are aligned at the same position in the axial direction.

The position L22 of the top sealing section 45 and the position L24 of the top sealing section 34 are substantially the same. Therefore, at the maximum insertion position of the sample pickup rod 14, the top sealing section 45 and the top sealing section 34 are aligned at the same position in the axial direction.

The outer diameter of the top sealing section 45 is set such that this section 45 is tightly fitted to the inner circumference of the top sealing section 34.

The position L25 of the top end 46 of the sample pickup rod 14 is set shorter than the position L26 of the top end 48 of an inner space 47 of the small diameter section 18. Therefore, at the maximum insertion position, a gap L26−L25 is formed between both the top ends 46 and 48.

The top end portion 52 of the large diameter holding section 36 of the sample pickup rod 14 has a dimension allowing the top end portion 52 to be tightly fitted to the inner circumference of the bottom end portion 51 of the bottle main body 6.

Next, the sampling bottle constructed as above will be described how it is treated in use.

The sample pickup rod 14 is dismounted from an assembly of the bottle main body 6, inner plug 13, and sample pickup rod 14. Then, the small diameter pickup rod section 35 of the sample pickup rod 14 is pierced into sample dejection and pulled out of it. The sample pickup rod 14 with sample dejection being attached thereto is inserted into the inner plug 13.

In the course of inserting the sample pickup rod 14 up to the maximum insertion position, the excessive sample attached to the outer periphery of the sample pickup rod 14 is scraped off by the annular scrape section 33b. The scraped, excessive sample is accommodated within an excessive sample room 50 between the large diameter section 16 of the inner plug 13 and the small diameter pickup rod section 35 of the sample pickup rod 14. There are only a predetermined quantity of sample held in the sample holding section 43 of the sample pickup rod 14, and an excessive sample attached to the top end of the small diameter pickup rod section 35.

When the small diameter pickup rod section 35 reaches the maximum insertion position, the sample holding section 43 is aligned with the windows 24 of the inner plug 13. In this state the sample attached to the top end 46 of the small diameter pickup rod section 35 is sealed within the inner space 47 of the inner plug 13. The opposite ends in the axial direction of the excessive sample room 50 are closed by the abutment of the scrape section 33b with the small diameter pickup rod section 35, so that the excessive sample is liquid tightly sealed within the excessive sample room 50.

In this manner, only the predetermined quantity of the sample held at the sample holding section 43 becomes in contact with test liquid 2 and is suspended within it. IN this state wherein the sample pickup rod 14 is inserted into the inner plug of the bottle main body 6 up to its maximum insertion position, the top end portion 52 of the large diameter holding section 36 of the sample pickup rod 14 is tightly fitted to the inner surface of the bottom end portion 51 of the bottle main body 6.

Figure 8:
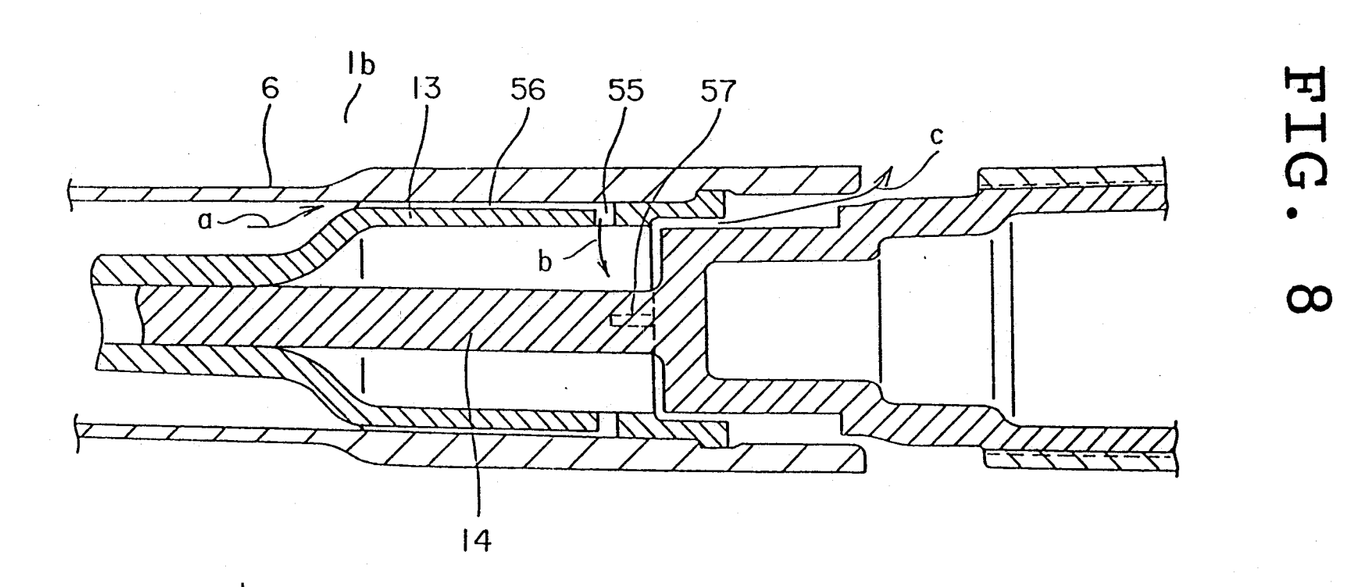
FIG. 8 is a lateral cross sectional view of a sampling bottle when a sample pickup rod is inserted to an intermediate position.

In the above manner, it is possible to make only the predetermined quantity of the sample held at the sample holding section 43 contact with test liquid 2 and be suspended in it. By piercing a pin or the like through the thin wall 3 at the outlet of the nozzle unit 4, this sample-suspended solution can be discharged out of the bottle main body after passing through the filter 11. Air within the bottle main body 6 pushed while inserting the sample pickup rod 14, is ejected out from the bottom end 15 of the inner plug 13, via the air vent 54, i.e., the communicated external groove 56, through holes 55 and internal grooves 57, as shown by arrows a, b, and c shown in FIG. 8. Immediately before the small diameter pickup rod section 35 reaches the maximum insertion position, the through holes 55 are shut by the sample pickup rod 14. Then, the path for the air vent 54 is shut off and the internal space of the bottle main body 6 is sealed.

According to the sample bottle of this invention, the excessive sample attached to the outer surface of the sample pickup rod 14 inserted into the bottle main body 6 containing test liquid 2, is scraped off by the scrape section and sealed within the excessive sample room 50 between the inner plug 13 and the sample pickup rod 14. The excessive sample attached to the top end of the sample pickup rod 14 is sealed within the top inner space of the inner plug 13. Accordingly, only the predetermined quantity of the sample held in the sample holding section 43 can contact with the test liquid 2 and suspended in it.

As described above, a good quantitative precision of sample can be realized. Excessive sample is sealed within the excessive sample room 50 and the inner space 47 of the inner plug 13. Therefore, the excessive sample will not be suspended in test liquid 2 and leaked externally. Furthermore, the room and space for sealing excessive sample are formed by the two members, inner plug 13 and sample pickup rod 14, allowing a simple structure of sealing.

More important is that air within the bottle main body 6 pushed while inserting the sample pickup rod 14, continues to be ejected out, via the communicated external groove 56, through holes 55 and internal grooves 57 immediately before the small diameter pickup rod section 35 reaches the maximum insertion position. Therefore, air within the bottle main body 6 will not be compressed and will not take a positive pressure, preventing scattering suspended solution when opening the sampling bottle and pushing back sample dejection out of the bottle main body 6.

As appreciated from the foregoing description of the present invention, it is possible to provide a sampling bottle with easy handling of dejection sample, simple structure, reliable prevention of scattering dejection sample and propagation of offensive smell to nearby environments, and good quantitative precision.

I claim:

1. A sampling bottle comprising:
a bottle main body having an open bottom end and a nozzle unit closed by a thin wall capable of being opened, said bottle main body being capable of containing test liquid;
a sample holding unit insertable into said bottle main body from said open bottom end;
said sample holding unit having an inner plug and a sample pickup rod;
said inner plug being of a tubular shape having a large diameter section adapted to be liquid tightly fitted to an inner surface of a torso section of said bottle main body and a small diameter section having an outer diameter smaller than said large diameter section, both being integrally coupled via a first shoulder section a first top end of said small diameter section being closed and a first bottom end of said large diameter section being open, and at least one window being formed in a wall of said small diameter section between said first top end and a bottom end of said small diameter section;
an inner surface of said small diameter section of said inner plug being formed with an annular projection on the bottom end of said small diameter section, and a first scrape section and a top sealing section adjacent said at least one window are located adjacent the at lest one window of the small diameter section, thereby defining in cooperation with each other a border of said at least one window,
said sample pickup rod having a small diameter pickup rod section and a large diameter holding section, both integrally coupled in the axial direction via a second shoulder section, said pickup rod section having a projection adjacent said annular projection in a maximum insertion position of said sample pickup rod in said inner plug and said pickup rod section having a sample pickup section at a top end portion of said pickup rod section, said sample pickup section comprising a sample holding section of a one-side open recess and said pickup rod section having a second scrape section and a second top sealing section both located adjacent said sample holding section, thereby defining in cooperation with each other a border of the sample holding section,
wherein at the maximum insertion position of said sample pickup rod in said inner plug, said first scrape section of said inner plug contacts said second scrape section of said sample pickup section of said pickup rod section to close an end of an annular excessive sample room formed in the axial direction between the inner surface of said inner plug and the outer surface of said pickup rod section, and said first top sealing section liquid tightly seals a top end of said pickup rod section within a space formed at a top end portion of said inner plug.

2. A sampling bottle according to claim 1, wherein said bottle main body is formed adjacent said open bottom end of said bottle main body with a positioning step, the outer diameter of said small diameter section of said inner plug is smaller than the inner diameter of said torso section of said bottle main body, the outer diameter of said large diameter section is set such that said large diameter section is fluid tightly fitted to the inner diameter of said torso section of said bottle main body, said large diameter section forms at the outer surface thereof a groove having a third open top end and a third closed bottom end in the axial direction, and a positioning flange ring is formed by extruding at said first open bottom end of said large diameter section, and wherein the insertion position of said inner plug into said bottle main body is defined by abutment of said positioning flange ring with said positioning step of said bottle main body.

3. A sampling bottle according to claim 1, wherein said second scrape section provides a scraping means for excessive sample by being adapted to tightly contact against an inner surface of said first scrape section at said maximum insertion position of the sample pickup rod in said inner plug and said second top sealing section providing sealing means being adapted to tightly contact against the inner surface of said first top sealing section at the maximum insertion position of the sample pickup rod in said inner plug.

4. A sampling bottle comprising
a bottle main body having a first open bottom end and a nozzle unit closed by a thin wall capable of being opened, said bottle main body being capable of containing test liquid, and
a sample holding unit insertable into said bottle main body from said first open bottom end,
said sample holding unit having an inner plug and a sample pickup rod,
said inner plug being of a tubular shape having a large diameter section adapted to be liquid tightly fitted to an inner surface of a torso section of said bottle main body and a small diameter section having an outer diameter smaller than said large diameter section, both being integrally coupled via a first shoulder section, a second top end of said smaller diameter section being closed and a second bottom end of said large diameter section being open, and at least one window being formed in a wall of said small diameter section between said second top end and a bottom end of said small diameter section,
the inner surface of said small diameter section of said inner plug being formed with a scrape section between said second top end of said small diameter section of said inner plug and said at least one window and a top sealing section,
said sample pickup rod having a small diameter pickup rod section and a large diameter holding section, both integrally coupled in the axial direction via a second shoulder section, said pickup rod section having a sample pickup section at a top end portion, said sample pickup section comprising a one-side open recess, said sample pickup section has a dimension allowing a liquid tight fit to said scrape section of said inner plug, and said large diameter section of said inner plug being formed with an air vent, wherein at maximum insertion position of said sample pickup rod in said inner plug, said scrape section of said inner plug contacts said sample pickup section of said sample pickup rod to close the end of an annular excessive sample room formed in the axial direction between the inner surface of said inner plug and the outer surface of said pickup rod section, and said top sealing section liquid tightly seals a top end of said pickup rod section within a space formed at the second top end of said inner plug.

5. A sampling bottle according to claim 4, wherein said bottle main body is formed adjacent said first open bottom end thereof with a positioning step, the outer diameter of said small diameter section of said inner plug is smaller than the inner diameter of said torso section of said bottle main body, the outer diameter of said large diameter section is set such that said large diameter is fluid tightly fitted to the inner diameter of said torso section of said bottle main body, at least one through hole is formed in said large diameter section, an external groove is formed over the outer surface of said large diameter section, said external groove being open at the first top end in the axial direction and communicated with said at least one through hole at the first bottom end in the axial direction, and at least one internal groove is formed on the inner surface of said large diameter section, said external groove being closed near said through hole at the first top end in the axial direction and communicating with said second open bottom end of said large diameter section in the axial direction, and a positioning ring flange is formed by extruding at said second open bottom end of said large diameter section, and wherein the insertion position of said inner plug into said bottle main body is defined by abutment of said positioning ring flange with said positioning step of said bottle main body.

* * * * *